United States Patent [19]

Gary et al.

[11] 3,998,761

[45] Dec. 21, 1976

[54] SHAMPOO COMPOSITIONS CONTAINING BEER SOLIDS

[75] Inventors: Herbert H. Gary, Edison; William Bess, Lindhurst; Frederick Hubner, Edison, all of N.J.

[73] Assignee: Bristol-Myers Company, New York, N.Y.

[22] Filed: Apr. 17, 1975

[21] Appl. No.: 569,328

Related U.S. Application Data

[63] Continuation of Ser. No. 372,551, June 22, 1973, abandoned.

[52] U.S. Cl. .............................. 252/544; 252/89 R; 252/DIG. 13; 424/70
[51] Int. Cl.² ...................... C11D 3/26; A61K 7/08
[58] Field of Search ............ 252/544, DIG. 13, 89, 252/550, 558; 424/70

[56] References Cited

UNITED STATES PATENTS 2,826,551  3/1958  Green ................................ 252/89

FOREIGN PATENTS OR APPLICATIONS 6,712,816  0000  Netherlands ...................... 252/89
782,081  8/1957  United Kingdom ................. 252/89

OTHER PUBLICATIONS

American Perfumer, vol. 77, 1/62, p. 8.

Primary Examiner—William E. Schulz
Attorney, Agent, or Firm—Irving Holtzman; George A. Mentis; David J. Mugford

[57] ABSTRACT

Shampoo compositions capable of conditioning hair containing relatively high quantities of beer solids as hair conditioning agents.

7 Claims, No Drawings

SHAMPOO COMPOSITIONS CONTAINING BEER SOLIDS

This is a continuation of application Ser. No. 372,551, filed June 22, 1973 and now abandoned.

This invention relates to shampoo compositions which are suitable for shampooing and conditioning human hair. More particularly, it concerns shampoo compositions containing as an essential conditioning ingredient a relatively high level of beer solids.

It has been suggested in the prior art to add whole beer to a shampoo. In this connection, attention is respectfully directed to Amer. Perf. 77:8 (January 1962). Since the beer is added as whole beer, the quantity of beer solids that are added to these shampoos is very small. It has been found, however, that shampoo compositions containing relatively high amounts of beer solids provide a product that when used to shampoo human hair leaves the hair in unexpected bodied and conditioned state. This is accomplished by incorporating in the shampoo compositions beer solids to the extent of about 4% to 20% by weight and preferably, between about 6% and 9% by weight based on the total weight of the shampoo compositions.

In accordance with the present invention, the beer solids are added to the shampoo compositions in the form of a beer concentrate which comprises between about 50% to 70% by weight of beer solids in liquid beer. A source of said beer concentrate that is especially suited for the present purposes and which is employed in the Examples given below is derived from a by-product beer fraction produced in the conventional beer manufacturing procedure. Following the fermentation step in the preparation of beer, it is customary to first convey the liquid beer to a tank in which it is then subjected to a clarification procedure to precipitate the proteins, as for example, by the addition of tannins. This produces a top layer of clear beer which is decanted and sent to the bottling stage and a bottom liquid sludge layer.

This latter bottom layer which often has been discarded in the past is now subjected to a separation procedure (e.g. centrifuging) to produce a liquid layer and a solid layer. The liquid layer is separated from the solid layer and then concentrated by evaporation of the liquid to produce a beer concentrate which has a solid content in the range of from about 50% to 70%. This beer concentrate may then be employed as the source of concentrated beer solids in the shampoo compositions of this invention.

The second essential ingredient of the present shampoo compositions is the detergent system. This will comprise one or more detergents which will ordinarily be synthetic detergents. Typical among the detergents that may be used herein, mention may be made of the alkyl benzene sulfonates, primary alkyl sulfates, secondary alcohol sulfates, alkyl benzene polyoxyethyl sulfonates, sulfated monoglycerides, sulfonated oils; nonionics e.g. Triton X-100, Igepals, Myrjs, Pluronics, etc. Synthetic detergents that may be used herein are further illustrated on pages 393 through 402 of "Cosmetics Science and Technology" by Edward Sagarin, Interscience Publishers, Inc., New York, 1957 which pages are incorporated herein by way of reference.

The quantity of detergent that may be incorporated in the present composition may vary. Ordinarily, however, it will constitute between 10 to 20% by weight based on the total weight of the composition.

In addition to the aforesaid ingredients, the present shampoo compositions may also include other ingredients usually found in conventional shampoo compositions. Typical among these are opacifying agents, clarifying agents, finishing agents, sequestering agents, thickening agents, foam builders, activators, preservatives, optical bleaches, builders, antibacterials, antidandruff compounds, etc. These agents that may be used in the present compositions are further illustrated at pages 403 through 408 in Sagarin cited above. These pages are incorporated in the present specification by way of reference.

The following Examples are given to further illustrate the present invention. It is to be understood, however, that this invention is not limited thereto.

In the Example given below the following terms have the meanings defined below:

Beer Concentrate (50%): This is a beer concentrate prepared in the manner described above and comprising 50% beer solids in liquid beer. The solids comprise a mixture of proteins and polysaccharides. The proteins have the following molecular weight distribution M.W. 23,000 — 35%; M.W. 36,500 — 32%; M.W. 68,000 — 10%; balance polypeptides 23%; and consisting of the following amino acids: aspartic, glutamic, alanine, isoleucine, phenylalanine, arginine, threonine, proline, valine, leucine, lysine, serine, glycine, methionine, tyrosine and histidine. The polysaccharides are a mixture of polysaccharides containing upward of one glucose unit per molecule. Of these about 50% by weight comprise polysaccharides containing 1 to 9 glucose units per molecule; the balance being made up of polysaccharides containing 10 or more glucose units per molecule.

| Preserved 3.5% Hydroxypropyl Methylcellulose Mucilage: | |
|---|---|
| Formaldehyde solution, 37% | 0.25 |
| Hydroxypropyl methylcellulose, 4000cps (Methocel 60 HG 4000 cps) | 3.50 |
| Water, deionized | 96.25 |
| | 100.00 |

Preparation of 3.5% Hydroxypropyl Methylcellulose Mucilage (Preserved with 0.25% formaldehyde Solution 37%):

Heat 25% of the formula weight of water to 185°–190° F and slowly disperse the hydroxypropyl methylcellulose powder under rapid lightning agitation. Stir for 10–15 minutes.

Mix 0.25% formaldehyde solution (37%) with the remaining 71.25% water which has been precooled to 32° F. Add this solution to the dispersed hydroxypropyl methylcellulose water mixture and agitate until a lump-free mucilage is obtained. It is recommended that the mucilage be prepared a day prior to use.

EXAMPLE 1

| Ingredients | % by weight |
|---|---|
| Water, deionized | 26.32 |
| methylparaben | 0.25 |
| Propylparaben | 0.05 |
| Sodium lauryl sulfate, 60% (Standapol CS) | 3.00 |
| Sodium Polyoxyethylene (1) lauryl | |

-continued

EXAMPLE 1

| Ingredients | % by weight |
|---|---|
| ether sulfate (Sipon ESY) containing 0.10% formaldehyde solution | 45.00 |
| Disodium edetate, dihydrate | 0.05 |
| Citric acid, anhydrous, pwd. | 0.18 |
| Methyl diethyl polyoxypropylene (8) ammonium chloride (Emcol CC-9) | 2.00 |
| Preserved hydroxypropyl methylcellulose mucilage (3.5%) | 5.00 |
| Lauric myristic (70–30) diethanolamide (Monamid 150 LMW-C) | 5.00 |
| Perfume Agreste 45/2 (Charabot) | 0.07 |
| Perfume Herbal 63/53 (Charabot) | 0.30 |
| Beer Concentrate, 50% (Anheauser-Busch) | 12.00 |
| Formaldehyde solution, 37% | 0.15 |
| | 100.00 |

Procedure:

A. In a stainless steel, steam-jacketed kettle, of suitable size to contain the entire batch, weigh in the formula weight of water and heat to 170° F. Add the methylparaben and propylparaben and mix until dissolved (10–15 minutes). Individually add the sodium lauryl sulfate, sodium polyoxyethylene (1) lauryl ether sulfate, disodium edetate dihydrate, citric acid, methyl diethyl polyoxypropylene (8) ammonium chloride, and mix until uniform (15–20 minutes). Cool the batch slowly to 105°–110° F and add the hydroxypropyl methylcellulose mucilage and continue agitation.

B. In a separate stainless steel, steam-jacketed kettle, melt the lauric-myristic (70–30) diethanolamide by heating to 130° F. Add the perfumes and mix 5 minutes just prior to Step C.

C. Slowly add the oil phase (B) at 130° F to the aqueous phase and agitate until clear and uniform (15–20 minutes).

D. Incorporate the beer concentrate and cool slowly to 85°–90° F. Add the formaldehyde solution and adjust for water loss, if necessary.

| | |
|---|---|
| Appearance: | Slightly hazy, viscous liquid |
| Color: | Amber |
| Fragrance: | Herbal-Lavender-Pine |
| pH: | 6.3 ± 0.3 (adjust with citric acid if necessary) |
| Viscosity: | 24 hours - 1750 ± 250 cps No. 3 spindle 20 rpm - 15 seconds |
| Density: | 1.05 ± 0.05 g/cc |

EXAMPLE 2

The procedure and ingredients employed in Example 1 above are followed, except that in place of the beer concentrate 50%, a beer concentrate made in the same fashion as described above but containing 62.0% beer solids is employed. The proteins contained in this concentrate have the same molecular weight distribution and are made of the same amino acids at those found in the beer concentrate (50%). In addition, this concentrate has the following analysis:

| Percent Solids | Percent Protein 6.25 × Nitrogen | Percent Total | Carbohydrates Di, Tri, etc. Polysaccharides | |
|---|---|---|---|---|
| 62.0 | 4.90 | 43.1 | $G_1$ | 0.33 |
| | | | $G_2$ | 1.60 |
| | | | $G_3$ | 3.10 |
| | | | $G_4$ | 3.57 |
| | | | $G_5$ | 1.72 |
| | | | $G_6$ | 2.42 |
| | | | $G_7$ | 2.37 |
| | | | $G_8$ | 3.58 |
| | | | $G_9$ | 3.40 |
| | | | $G_{10}$ and above | 22.0 |

The percentages shown are reported on the basis of the beer concentrate and not on the basis of total solids in the concentrate. $G_1$, $G_2$, etc. refer to the number of glucose units contained in the carbohydrate fraction.

What is claimed is:

1. A shampoo composition suitable for conditioning hair comprising at least one detergent and a waste liquid beer sludge concentrate distributed in an aqueous medium, the beer solids contained in said composition comprising from about 4% to 20% by weight based on the total weight of the shampoo composition and wherein said detergent comprises about 10 to 20% based on the total weight of the composition.

2. A shampoo composition according to claim 1 wherein the beer solids contained in said composition range from about 6% to 9% by weight based on the total weight of the shampoo composition.

3. The composition of claim 2 wherein the detergent is sodium polyoxyethylene (1) lauryl ether sulfate.

4. The composition of claim 1 including sodium lauryl sulfate.

5. The composition of claim 1 including lauric-myristic (70–30) diethanolamide.

6. A composition according to claim 1 including methyl diethyl polyoxypropylene (8) ammonium chloride.

7. A shampoo composition suitable for conditioning hair comprising at least one detergent and a waste liquid beer sludge concentrate distributed in an aqueous medium, the beer solids contained in said composition comprising from about 4% to 20% by weight based on the total weight of the shampoo composition, said detergent comprising about 10% to 20% by weight based on the total weight of the composition and selected from the group consisting of alkyl benzene sulfonates, primary alkyl sulfates, secondary alcohol sulfates, alkyl benzene polyoxyethyl sulfonates, sulfated monoglycerides, sulfonated oils, alkylphenoxypoly (ethyleneoxy) ethanols, polyoxyalkylene fatty acid esters, condensates of ethyleneoxide with hydrophobic bases formed by condensing propyleneoxide and propylene glycol.

* * * * *